United States Patent [19]

Morgan

[11] Patent Number: 5,543,308
[45] Date of Patent: Aug. 6, 1996

[54] ISOLATED DNA ENCODING THE FSEI RESTRICTION ENDONUCLEASE AND RELATED METHODS FOR PRODUCING THE SAME

[75] Inventor: Richard D. Morgan, Middleton, Mass.

[73] Assignee: New England Biolabs, Inc., Beverly, Mass.

[21] Appl. No.: 325,509

[22] Filed: Oct. 18, 1994

[51] Int. Cl.$^6$ .......................... C12N 9/22; C12N 15/55; C12N 15/70
[52] U.S. Cl. .................. 435/172.3; 435/199; 435/320.1; 435/252.33; 536/23.2
[58] Field of Search ................................ 435/172.3, 199, 435/193, 320.1, 252.33; 536/23.2

[56] References Cited

U.S. PATENT DOCUMENTS 5,200,333 4/1993 Wilson ................................ 495/172.3
5,371,006 12/1994 Morgan et al. ......................... 435/194

FOREIGN PATENT DOCUMENTS

90/13653 11/1990 WIPO.

OTHER PUBLICATIONS

Prieto et al., J. Cell. Biol. 119: 663–678, 1992.
Lord et al., J. Biol. Chem. 265: 838–843, 1990.
Sekiguchi et al., Essays in Biochemistry 26: 39–48, 1991.
Kosykh, et al., Molec. Gen. Genet. 178:717–719 (1980).
Mann, et al., Gene, 3:97–112 (1978).
Walder, et al., Proc. Natl. Acad. Sci., 78:1503–1507 (1981).
Bougueleret, et al., Nucl. Acid. Res., 12:3659–3676 (1984).
Gingeras and Brooks, Proc. Natl. Acad. Sci. USA, 80:402–406 (1983).
Theriault and Roy, Gene, 19:355–359 (1982).
Blumenthal, et al., J. Bacteriol., 164:501–509 (1985).
Kiss, et al., Nucl. Acid. Res. 13: 6403–6421 (1985).
Szomolanyi, et al., Gene, 10:219–25 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Piekarowicz, et al., Nucleic Acids Res., 19:1831–1835 (1991).
Piekarowicz, et al., J. Bacteriology, 173:150–155 (1991).
Xu, et al., Nucleic Acids Res., 22:2399–2403 (1994).
Lunnen, et al., Gene, 74(1):25–32 (1988).
Raleigh and Wilson, Proc. Natl. Acad. Sci., USA, 83:9070–9074 (1986).
Heitman and Model., J. Bact., 169:3243–3250 (1987).
Raleigh, et al., Genetics, 122:279–296 (1989).
Waite–Rees, et al., J. Bateriology, 173:5207–5219 (1991).
Wilson, Methods in Enzymology 216:259–279 (1992).
Wilson, Nucl. Acids Res., 19: 2539–2566 (1991).
Nelson, et al., Nucl. Acids Res., 18:2061–2604 (1990).

Primary Examiner—Charles L. Patterson, Jr.
Attorney, Agent, or Firm—Gregory D. Williams

[57] ABSTRACT

The present invention is directed to a method for cloning and producing the FseI restriction endonuclease by 1) introducing the restriction endonuclease gene from Frankia species into a host whereby the restriction gene is expressed; 2) fermenting the host which contains the plasmid encoding and expressing the FseI restriction endonuclease activity, and 3) purifying the FseI restriction endonuclease from the fermented host which contains the plasmid encoding and expressing the FseI restriction endonuclease activity.

8 Claims, 5 Drawing Sheets

The DNA of *Frankia species* is purified.

The *Fse*I restriction endonuclease protein is purified to homogeneity.

Amino acid sequence at the *Fse*I endonuclease N-terminus is determined.
Degenerate DNA primers based on the amino acid sequence are synthesized.

Cytosine methylase amino acid sequences are compared for conserved motifs. Degenerate DNA primers based on conserved motifs are synthesized.

A portion of the endonuclease and methylase genes is amplified from *Frankia species* DNA by PCR techniques.

The sequence at the ends of the amplified DNA is determined.

The *Fse*I endonuclease gene is amplified from *Frankia species* DNA and cloned into an expression system.

The expressed *Fse*I endonuclease clone is grown in a fermenter in a rich medium with the appropriate antibiotic selection and induction.

The *Fse*I endonuclease is purified by standard protein purification techniques.

FIG. 1A

FIG. IB pRMFseR1 cloned DNA pRMFseR2 cloned DNA

Amino acid Sequence to mRNA (DNA) Sequence

| 1 letter code | G | A | V | L | I | S | T | D | N | E | Q | K | P | H | R | F | Y | W | C | M |
|---|---|---|---|---|---|---|---|---|---|---|---|---|---|---|---|---|---|---|---|---|
| 3 letter code | Gly | Ala | Val | Leu | Ile | Ser | Thr | Asp | Asn | Glu | Gln | Lys | Pro | His | Arg | Phe | Tyr | Trp | Cys | Met |
| mRNA 5' | GGA | GCA | GUA | CUA | AUA | UCA | ACA | GAC | AAC | GAA | CAA | AAA | CCA | CAC | CGA | UUC | UAC | UGG | UGC | AUG 3' |
| | C | C | C | C | C | C | C | U | U | G | G | G | G | U | C | U | U | | U | |
| | G | G | G | G | U | G | G | | | | | | G | | G | | | | | |
| | U | U | U | U | | U | U | | | | | | U | | U | | | | | |
| | | | | or UUA G | | or AGC U | | | | | | | | | or AGA G | | | | | |

Special signals
RNA
UAA = Ochre
UAG = Amber
UGA = terminate

Amino Acid Special Symbls
B = D or N
Z = E or Q

Ambiguous nucleotide abbrevations
These abbreviations conform to the IUPAC-IUB standard abbreviations.

```
      A  C  G  U/T
U/T =           U    Uracil/Thymine
G   =        G       Guanine
K   =        G   U
C   =    C           Cytosine
Y   =    C       U   Pyrimidine
S   =    C   G
B   =    C   G   U
A   = A              Adenine
W   = A          U
R   = A      G       Purine
D   = A      G   U
```

FIG. 6

ISOLATED DNA ENCODING THE FSEI RESTRICTION ENDONUCLEASE AND RELATED METHODS FOR PRODUCING THE SAME

BACKGROUND OF THE INVENTION

The present invention relates to recombinant DNA which encodes the FseI restriction endonuclease and modification methylase, and the production of these enzymes from the recombinant DNA.

Restriction endonucleases are a class of enzymes that occur naturally in bacteria. When they are purified away from other contaminating bacterial components, restriction endonucleases can be used in the laboratory to cut DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the recognition sequence. Different restriction endonucleases have affinity for different recognition sequences. More than one hundred different restriction endonucleases have been identified among the many hundreds of bacterial species that have been examined to date.

Bacteria tend to possess only a small number of restriction endonucleases per species. The endonucleases typically are named according to the bacteria from which they are derived. Thus, the species *Neisseria lactamica* for example, synthesizes four different restriction endonucleases, named NlaI, NlaII, NlaIII and NlaIV. These enzymes recognize and cleave the sequences GGCC, GATC, CATG and GGNNCC respectively. *Escherichia coli* RY13, on the other hand, synthesizes only one enzyme, EcoRI, which recognizes the sequence GAATTC.

While not wishing to be bound by theory, it is thought that in nature restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The cleavage that takes place disables many of the infecting genes and renders the DNA susceptible to further degradation by non-specific nucleases.

A second component of bacterial protective systems are the modification methylases. These enzymes are complementary to restriction endonucleases and provide the means by which bacteria are able to protect their own DNA and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is fully modified by virtue of the activity of its modification methylase, and is therefore insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins that they encode in greater quantities than are obtainable by conventional purification techniques. The standard approach to isolating clones of interest (restriction endonuclease genes) is to develop a simple and reliable method to identify such clones within complex 'libraries' i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Molec. Gen. Genet* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acid. Res.* 12: 3659–3676, (1984); PaeR7: Gingeras and Brooks, *Proc. Natl. Acad. Sci.* USA 80:402–406, (1983); Theriault and Roy, *Gene* 19:355–359 (1982); PvuII: Blumenthal et al., *J. Bacteriol.* 164: 501–509, (1985)).

A third approach, which is being used to clone a growing number of systems, involves selection for an active methylase gene (See e.g., U.S. Pat. No. 5,200,333 and BsuRI: Kiss et al., *Nucl. Acid. Res.* 13:6403–6421, (1985)). Since restriction and modification genes are often closely linked, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al, *Gene* 20: 197–204 (1982); BsuRI: Kiss and Baldauf, *Gene* 21: 111–119, (1983); and MspI: Walder et al., *J. Biol. Chem.* 258: 1235–1241, (1983)).

Another method for cloning methylase and endonuclease genes is based on a colorimetric assay for DNA damage. When screening for a methylase, the plasmid library is transformed into the host *E. coli* strain such as AP1-200. The expression of a methylase will induce the SOS response in an *E. coli* strain which is McrA+, McrBC+, or Mrr+. The AP1-200 strain is temperature sensitive for the Mcr and Mrr systems and includes a lac-Z gene fused to the damage inducible dinD locus of *E. coli*. The detection of recombinant plasmids encoding a methylase or endonuclease gene is based on induction at the restictive temperature of the lacZ gene. Transformants encoding methylase genes are detected on LB agar plates containing X-gal as blue colonies. (Piekarowicz, et.al., *Nucleic Acids Res.* 19:1831–1835, (1991) and Piekarowicz, et.al. *J. Bacteriology* 173:150–155 (1991)). Likewise, the *E. coli* strain ER1992 contains a dinD1-Lac Z fusion but is lacking the methylation dependent restriction systems McrA, McrBC and Mrr. In this system (called the "endo-blue" method), the endonuclease gene can be detected in the absence of it's cognate methylase when the endonuclease damages the host cell DNA, inducing the SOS response. The SOS-induced cells form deep blue colonies on LB agar plates supplemented with X-gal. (Xu et.al. Nucleic Acids Res. 22:2399–2403 (1994))

Sometimes the straight-forward methylase selection method fails to yield a methylase (and/or endonuclease) clone due to various obstacles. See, e.g., Lunnen, et al., *Gene,* 74(1):25–32 (1988). One potential obstacle to cloning restriction-modification genes lies in trying to introduce the endonuclease gene into a host not already protected by modification. If the methylase gene and endonuclease gene are introduced together as a single clone, the methylase must protectively modify the host DNA before the endonuclease has the opportunity to cleave it. On occasion, therefore, it might only be possible to clone the genes sequentially, methylase first then endonuclease.

Another obstacle to cloning restriction-modification systems lies in the discovery that some strains of *E. coli* react adversely to cytosine or adenine modification; they possess systems that destroy DNA containing methylated cytosine (Raleigh and Wilson, *Proc. Natl. Acad. Sci.,* USA 83:9070–9074, (1986)) or methylated adenine (Heitman and Model, *J. Bact.* 196:3243–3250, (1987); Raleigh, Trimarchi, and Revel, *Genetics,* 122:279–296, (1989) Waite-Rees, et al., *J. Bacteriology,* 173:5207–5219 (1991)). Cytosine-specific or adenine-specific methylase genes cannot be cloned easily into these strains, either on their own, or together with their corresponding endonuclease genes. To avoid this problem it is necessary to use mutant strains of *E. coli* (McrA$^-$ and McrB$^-$ or Mrr$^-$) in which these systems are defective.

A third potential difficulty is that some restriction endonuclease and methylase genes may not express in *E. coli* due to differences in the transcription machinery of the source organism and *E. coli,* such as differences in promotor and ribosome binding sites. The methylase selection technique requires that the methylase express well enough in *E. coli* to fully protect at least some of the plasmids carrying the gene.

Because purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

The present invention relates to recombinant DNA encoding the genes for the FseI restriction endonuclease and modification methylase obtainable from Frankia species (NRRL 18528) as well as related methods for the production of these enzymes from the recombinant DNA. This invention also relates to a transformed host which expresses the restriction endonuclease FseI, an enzyme which recognizes the DNA sequence 5'-GGCCGGCC-3' and cleaves in the recognition sequence between the second -GC- pair leaving a 4 base 3' overhang (FseI: Nelson et al., *Nucl. Acid. Res.* 18:2061–2064 (1990)). FseI restriction endonuclease produced in accordance with the present invention is substantially pure and free of the contaminants normally found in restriction endonuclease preparations made by conventional techniques.

As the methylase selection approach failed to yield a methylase clone, a novel approach was designed to clone the FseI restriction-modification system. The preferred method for cloning the FseI restriction-modification system consists of purifying the FseI endonuclease from Frankia species to near homogeneity, determining the amino acid sequence at the N-terminus of the protein, synthesizing degenerate DNA primers based on (1) the FseI endonuclease N-terminal amino acid sequence and (2) on conserved amino acid sequences of cytosine methylases and amplifying a portion of the endonuclease and methylase from genomic Frankia species DNA with these primers. The FseI endonuclease can then be expressed by amplifying the complete gene from Frankia species DNA and cloning it into an expression vector, such as pAII17 or pRRS. This construct is introduced into a host which is premodified at FseI sites by virtue of a heterologous methylase, such as NlaI, or the FseI methylase, carried on a separate compatible plasmid.

In order to clone the FseI methylase, and to alternatively express the FseI endonuclease, a library containing DNA from Frankia species is formed. Clones S5 containing the methylase and endonuclease genes are identified by hybridization to the amplified DNA obtained above. The cloned DNA is sequenced to determine the DNA sequence of the endonuclease and the methylase, and the methylase and endonuclease are separately amplified from the Frankia species genomic DNA and cloned into appropriate expression vectors. FseI is produced by growing the host containing the FseI endonuclease and either FseI or NlaI methylase genes, inducing with the appropriate expression conditions, harvesting the cells and purifying the FseI endonuclease.

BRIEF DESCRIPTION OF THE FIGURES

FIG. 6 is an explanation of the one letter code for amino acid sequence.

DETAILED DESCRIPTION OF THE INVENTION

Figure 1:
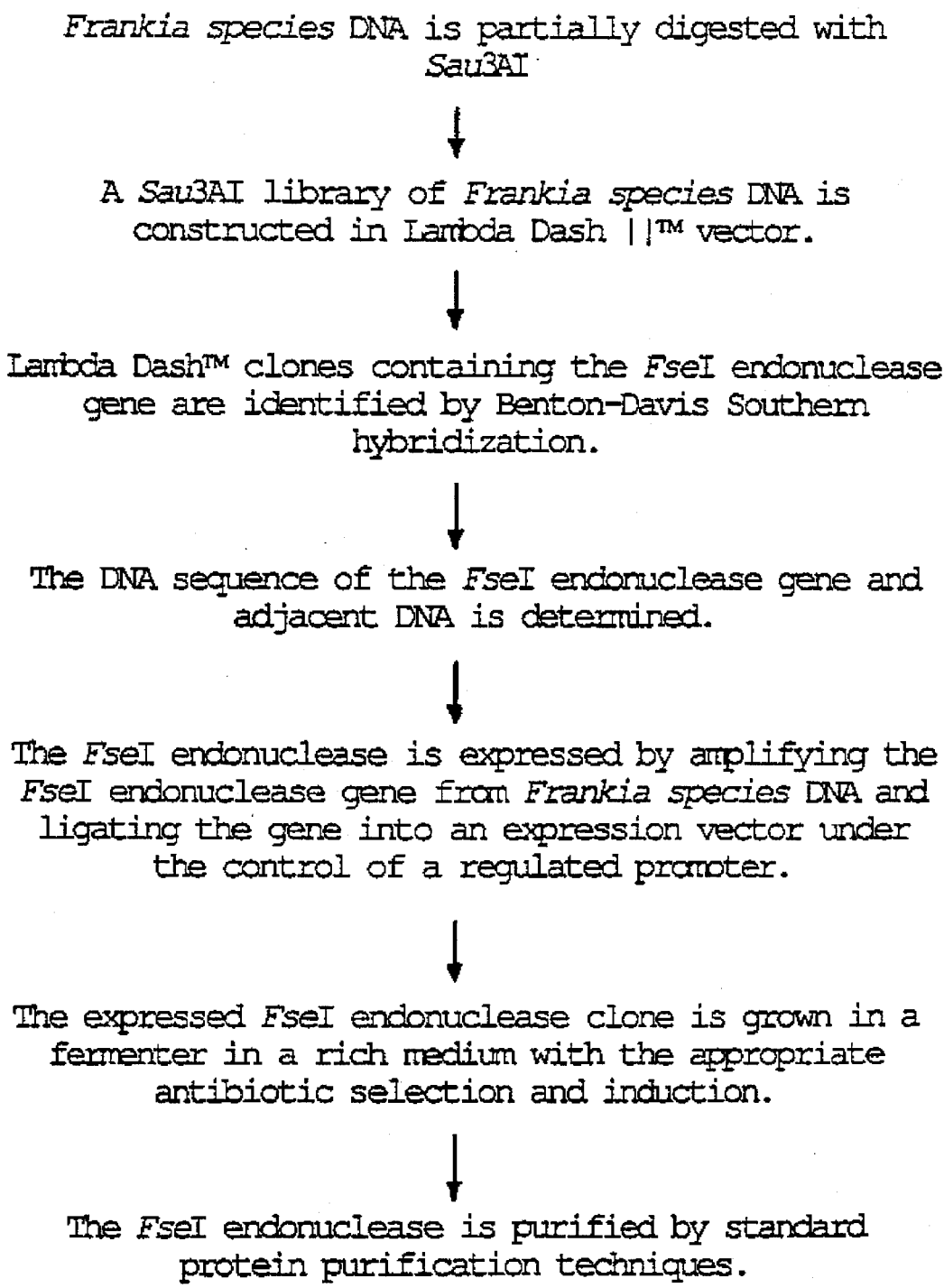
FIGS. 1A and 1B illustrates the preferred method for cloning and producing the FseI restriction endonuclease. At the onset of the cloning project, it was not known which strategies or conditions would be successful in cloning the FseI restriction-modification system. Indeed, the methylase selection approach did not yield FseI methylase (nor endonuclease) clones. The protein sequencing, methylase comparison, primer design, DNA amplification and the cloning results, and subsequent DNA sequencing, mapping, and characterization of the clones described in FIG. 1 and Example 1 reveal the previously unknown direct pathway for cloning and expressing the FseI restriction-modification system.
Figure 2:
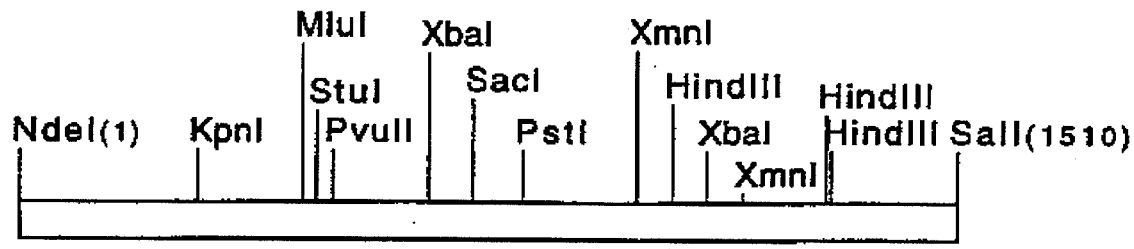
FIG. 2 is a restriction map of the DNA inserted into the vector pAII17 to create the over-expression clone pRMFseR1.
Figure 3:
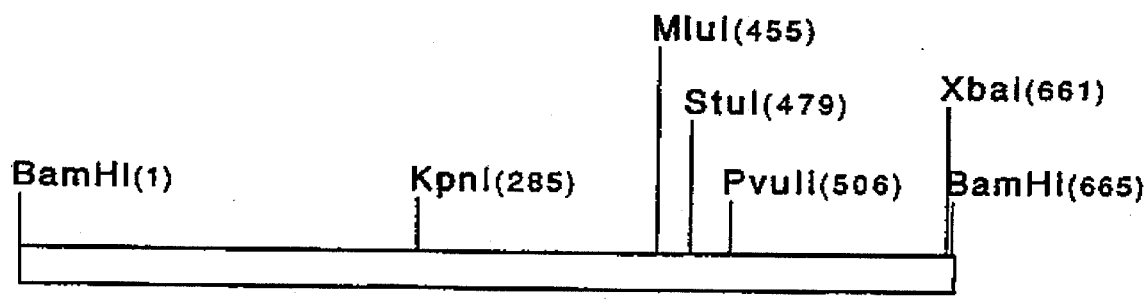
FIG. 3 is a restriction map of the DNA inserted into the vector pRRS to create the over-expression clone pRMFseR2.

The present invention relates to recombinant DNA which encodes the FseI restriction endonuclease and methylase, as well as to the enzymes produced from such a recombinant DNA.

The cloning of the FseI restriction endonuclease gene from Frankia species proved to be unusually difficult. No methylase clones were obtained by the standard methylase selection procedure, even though many different libraries were constructed and screened in both E. coli and Streptomyces host systems. This appears to be due to a failure of the FseI methylase to express in E. coli or Streptomyces at levels which would provide protection.

The FseI endonuclease was therefore cloned by a novel approach. The endonuclease protein was purified to near homogeneity and used to determine amino acid sequence at the amino-terminal end of the protein. Degenerate DNA primers based on the amino acid sequence of the N-terminal region were synthesized. In addition, the amino acid sequences of cytosine methylases were compared for conserved amino acid motifs, and degenerate DNA primers based on these conserved amino acid sequences were synthesized. Since the FseI recognition site contains only G and C basepairs, the FseI methylase must be a cytosine methylase and should contain some or other of the conserved amino acid motifs of cytosine methylases. (Given an endonuclease and methylase recognizing both adenine and cytosine bases, and for which the site of methylation is unknown, the same procedure should be effective in cloning the genes, although more primer combinations would need to be attempted to account for the adenine methylase conserved motifs as well.) A portion of the FseI methylase and FseI endonuclease genes was amplified using certain of the degenerate cytosine methylase primers in combination with the degenerate primers complementary to the N-terminus of the FseI endonuclease. An amplified DNA fragment of approximately 1650 bp was subcloned into pUC19 and sequenced. Amino acid sequence deduced from the DNA sequence of this PCR fragment matched the amino acid sequence of the FseI endonuclease in one region and matched conserved motifs of cytosine methylases in another region, confirming that this DNA fragment represented a portion of the FseI endonuclease gene and a contiguous cytosine methylase gene (subsequently shown to be the FseI methylase gene).

Since it was first discovered in accordance with the present invention that the entire FseI endonuclease gene coding sequence, with the exception of the first five amino acid codons, happened to be present on the 1650 bp PCR product, a rapid cloning strategy was attempted. A synthetic DNA primer was synthesized which had a restriction site at the ATG start codon to facilitate cloning, then had codons for the second through fifth amino acids as determined from the FseI endonuclease amino acid sequencing (codon usage biased for E. coli highly expressed gene codon usage), followed by sequences complementary to the DNA sequence as determined from the 1650 bp PCR product. This primer, along with a primer complementary to sequence of the 1650 bp PCR product known to be 3' of the FseI endonuclease gene (based on protein size) was used to amplify the FseI endonuclease gene. The amplified product was ligated into the pAII17 expression vector and introduced into a host pre-protected against FseI cleavage by the NlaI methylase gene cloned on a separate, compatible plasmid. Individual clones were examined and one which expressed the FseI endonuclease was used to produce FseI.

In order to determine and/or confirm the coding sequence for the beginning and end of the FseI endonuclease gene, clones containing the entire FseI endonuclease and methylase genes were obtained from Frankia species DNA without amplification to allow the determination of the DNA sequence of both genes. This would allow expression of the FseI methylase for protection, rather than using a methylase which modifies FseI and other sites (NlaI methylase methylares E. coli DNA in excess of 10,000 sites, whereas FseI methylase methylates between 10–20 sites), and confirmation of the amino acid sequence at the beginning of the FseI endonuclease. To this end a library of Frankia species DNA was constructed in a lambda-Dash vector system to generate clones containing 9 to 23 kb inserts of Frankia species DNA. The 1650 bp amplification product was used as a probe to identify lambda-Dash clones containing the endonuclease and methylase genes. These lambda clones were purified, their DNA extracted and digested with restriction enzymes to identify fragments from the clones of the same size as fragments identified by southern hybridization to Frankia species DNA. Two KpnI fragments, one of 1.8 kb and one of 7.0 kb, which together contained the entire FseI methylase and endonuclease genes and a 3.6 kb SacI fragment were subcloned from a lambda-Dash clone into pUC19 for easier manipulation. The DNA encoding the FseI endonuclease and methylase genes was sequenced and the exact nucleotide sequence at the N-terminus of the endonuclease gene was determined. It was found that the DNA sequence indicated the second amino acid residue of the FseI endonuclease was threonine, not histidine as originally thought from the protein sequence data. The original amino acid sequence call of histidine had been reported as questionable by the sequencer. Subsequent examination indicates a threonine residue is consistant with the amino acid sequencing data for this position, given the ambiguity in the data. The first clone, pRMFseR1, which expressed FseI endonuclease activity, thus had an inadvertant amino acid change at the second position without any noticible effect on enzyme function. We have therefore shown that we can produce a functionally active FseI endonuclease even with a non-conservative amino acid change.

The DNA sequence of the entire FseI endonuclease and methylase genes was determined from the 1.8 kb and 7.0 kb KpnI and 3.6 kb SacI clones. The FseI methylase was cloned into the vector pSYX20. Oligonucleotide primers designed to amplify the FseI methylase gene and facilitate its expression in the pSYX20 vector were synthesized, the methylase gene was amplified from Frankia species DNA, the amplified product was cleaved with the appropriate restriction enzymes and ligated into the pSYX20 vector previously cleaved with the same restriction endonucleases and transformed into ER2427 host cells. Individual transformants were picked and analyzed for the presence of the desired construct.

DNA primers were designed to amplify the entire FseI endonuclease gene. The forward primer had the following elements: a BamHI cloning site, stop codon in frame with the lacZ gene, E. coli consensus strong ribosome binding site, 7 nucleotide spacer sequence between the ribosome binding site and the ATG start codon of the FseI endonuclease, a correct threonine codon at the second position, a change of the codon for amino acid number 5 to an E. coli preferred codon and 24 nucleotides matching the FseI DNA sequence for hybridization. The 3' (reverse) primer was designed to hybridize just at the 3' end of the endonuclease gene, to minimize overlap with the methylase clone. A BamHI site was introduced in this primer to facilitate cloning. The endonuclease gene was amplified from the genomic Frankia species DNA. The amplified DNA was cleaved by BamHI and ligated into the expression vector pRRS, which had been previously cleaved by BamHI and dephosphorylated, and the ligation reaction was transformed into *E. coli* ER2427 competent cells carrying the NlaI methylase gene. Vectors containing inserts of the desired size were identified by miniprep procedures. These clones were grown to mid-log phase and induced with IPTG. The cells were then harvested by centrifugation, resuspended in sonication buffer and lysed by sonication. The extract was clarified and assayed for FseI endonuclease activity. One FseI expressing host was propagated and used to produce FseI restriction endonuclease. The FseI endonuclease was purified by standard protein purification techniques described herein below.

The method described herein by which the FseI restriction endonuclease and methylase genes are preferably cloned and expressed is illustrated in FIG. 1 and includes the following steps:

1. Frankia species is grown in flasks containing rich media, the cells are lysed and the genomic Frankia species DNA purified.

2. The FseI restriction endonuclease protein is purified to near homogeneity from Frankia species cells by a combination of protein purification techniques developed at New England Biolabs (see Example 1). The endonuclease so purified is nearly homogeneous on SDS polyacrylamide gel electrophoresis and has an apparent molecular weight of 28,000 daltons.

3. The amino terminal sequence of the endonuclease is obtained using an Applied Biosystems 470A Protein Sequencer (Brooks, et al., *Nucleic Acids Research*, 17:979–997, (1989)), and several degenerate DNA oligonucleotide primers are made based on the protein sequence. The amino acid sequence and the oligonucleotide primers derived from it are listed in the example.

4. The amino acid sequences of cytosine methylase genes are compared and areas of homology identified (Wilson, *Methods in Enzymology*, 216:259–279, (1992)). S0 Degenerate DNA primers are synthesized based on the amino acid sequence motifs of each type of cytosine methylase: 5-methyl cytosine, α-N4 cytosine and β-N4 cytosine methylases. The primers synthesized are listed in the example.

5. The cytosine methylase primers are used in combination with the FseI endonuclease N-terminal primers to amplify a portion of the FseI endonuclease and methylase genes from Frankia species DNA by PCR techniques. Various combinations of cytosine methylase primers and FseI endonuclease N-terminal primers are tried in PCR reactions to amplify part of the endonuclease and methylase genes. A linked endonuclease and methylase gene can occur in four possible combinations of relative positions: convergent, divergent, aligned endo first and aligned methylase first (Wilson, *Nucleic Acids Research*, 19:2539–2566, (1991)). Combined with the three possible types of cytosine methylases this makes twelve possible gene combinations. Primer combinations to account for all are tried. A prominent amplification product of approximately 1.5 kb is observed in the convergent gene position with a 5-methyl cytosine motif 4 forward primer plus an FseI endonuclease N-terminus forward primer, and a fainter product of 1.65 kb is observed with a 5-methyl cytosine motif 1 forward primer and the same N-terminus endonuclease primer. Using the 1.65 kb product as a template, the 1.5 kb product can be amplified with the motif 4 primer and the same FseI N-terminal primer. Both the 1.65 kb and 1.5 kb products are cloned into the vector pUC19.

6. DNA sequence at the ends of the PCR products of step 5 is determined. Amino acid sequence deduced from the DNA sequence agrees with the amino acid sequence of the FseI endonuclease determined in step 3 above. Also, amino acid sequence deduced from the other end of the amplified DNA contains amino acid motifs of 5-methyl cytosine methylases, and it is found that the 1.5 kb S5 product is an internal subset of the 1.65 kb product.

7. Overexpressing the FseI endonuclease gene:

A. General considerations: There are a number of ways in which the restriction gene can be overexpressed. The DNA sequence and detailed mapping information help determine the best approach for overexpression of the restriction endonuclease gene. One approach for overexpression comprises designing primers that hybridize directly at the N-terminus of the restriction endonuclease gene and somewhere downstream (3 prime) of the gene in order to use the polymerase-chain reaction to amplify the entire endonuclease gene. The resulting DNA fragment can be inserted into an expression vector such as pAII17 directly downstream of an inducible promoter (T7). Alternatively, overexpression can be accomplished by inserting a promoter recognized strongly by *E. coli*, such as $P_{tac}$ on pAGR3 (from W. Jack, New England Biolabs) directly in front of the beginning of the restriction endonuclease gene. This may be accomplished by finding convenient restriction sites near the beginning and end of the restriction endonuclease gene and compatible restriction sites near the promoter of pAGR3, and transferring the restriction gene into pAGR3 in line with the $P_{tac}$ promoter. Other regulated promoters which can be used are PlacUV5 (Fuller, *Gene* 19:43–54, (1982)), and 1PL (Shimatake and Rosenberg, *Nature* 254: 128, (1981)) on pUC19 and pBR322 derivatives. In addition, a strong ribosome binding site (Shine & Dalgarno, Proc. Natl. Acad. Sci. USA 71: 1342–1346, (1974)) can be placed in front of the gene to S0 increase expression. To obtain a stable clone which overexpresses the restriction endonuclease, the host is generally pre-protected from restriction endonuclease digestion. In the present invention this is accomplished by cloning in either the FseI methylase, or a heterologous methylase such as NlaI which protects from FseI digestion by modifying all FseI sites (as well as many other sites), on a separate plasmid. The plasmid used must be compatible with the expression vector. The methylase also must be produced at a level which will protect the host's genome from digestion by the overexpressed restriction endonuclease gene.

The DNA sequence of the gene can be altered by site-directed mutagenesis or by resynthesizing the gene itself to use codons that are more efficiently utilized in *E. coli* (Ikemura, *J. Mol. Biol.* 151:389–409, (1981)).

B. Initial rapid expression of FseI: Synthethic oligonucleotide primers are designed and used to amplify the FseI endonuclease gene from genomic Frankia species DNA for cloning into pAII17, a T7 expression vector. Using DNA sequence information from the 1650 bp PCR product above and the amino acid sequence of the FseI endonuclease, a synthethic oligonucleotide primer is constructed with an NdeI site (-CATATG-) positioned at the ATG start of the FseI endonuclease gene to facilitate cloning into the T7 expression vector pAII17 NdeI site, followed by DNA sequences coding for the first 5 amino acids of FseI as indicated from the amino acid sequence. Because of codon degeneracies considerations, the primer used to amplify the 1650 bp product above began at the codon for amino acid 6 of the FseI endonuclease protein sequence, and thus there was no DNA sequence information for amino acids 2 through 5 on which to base the expression primer. Therefore the primer sequence is chosen to incorporate the amino acids indicated for the first five positions in step 3 above, using the codons most frequently used in highly expressed *E. coli* genes. The expression primer then continues with 21 base pairs of sequence matching that of the 1650 bp PCR product. The reverse direction primer is chosen to match DNA sequence in the region of the cytosine methylase motif 4, because this will insure that the entire endonuclease gene is present, and because a convenient SalI restriction site can be created in this primer with only a one base pair change from the Frankia species DNA sequence. The amplified DNA is cleaved with NdeI and SalI and ligated into the vector pAII17 previously cleaved with NdeI and SalI. The ligated vector is introduced into an appropriate host, *E. coli* ER2417, carrying the inducible T7 polymerase gene and which has been pre-modified at FseI sites by virtue of expression of the NlaI methylase gene carried on the compatible vector pSYX20. Individual transformants are analyzed and one expressing FseI endonuclease is used for production of the enzyme.

8. Production: The FseI endonuclease may be produced from clones carrying the NlaI methylase gene (or the FseI methylase gene) and the overexpressed FseI restriction endonuclease gene by propagation in a fermenter in a rich medium with the appropriate antibiotic selection and induction. The cells are thereafter harvested by centrifugation and disrupted by sonication to produce a crude cell extract containing FseI restriction endonuclease activity.

9. Purification: The crude cell extract containing the FseI endonuclease is purified by a combination of standard protein purification techniques, such as affinity-chromatography or ion-exchange chromatography.

Further characterization of the FseI endonuclease and methylase and alternative expression of the enzymes:

10. The Frankia species DNA is digested completely and/or partially with a restriction endonuclease such as Sau3AI, or any of its isoschizomers, that cleaves to produce a fragment (s), cloneable in lambda-Dash II or any similar vector, which contains the entire FseI endonuclease and/or methylase genes.

11. The digested DNA's are ligated to the lambda phage cloning vector. The resulting mixtures are packaged in vitro and used to infect an appropriate host, such as *E. coli* strain ER1458 (NEB# 401-C). The titer of infect ire phage is determined by plating a portion of the packaged phage and counting the resultant plaques.

12. The in vitro packaged phage are preferably plated at varying densities in a soft agar lawn of an appropriate *E. coli* host, such as ER1458 (NEB# 401-C) on rich media. After incubation, phage containing the FseI endonuclease and methylase genes are identified by Benton-Davis Southern hybridization, using the PCR derived 1650 bp portion of the genes as probe against nitrocellulose filter lifts of the plaques. Positive plaques are removed from the plates and purified by several successive rounds of plating and hybridization. Positive clones are grown and their DNA purified.

13. A map of restriction fragments of Frankia species DNA in the region of the FseI endonuclease and methylase is produced by Southern hybridization of the 1650 bp PCR product probe against genomic Frankia species DNA digested with various restriction enzymes. An 1800 bp and 7000 bp KpnI fragment and a 3600 bp SacI fragment common to several lambda-Dash clones and the Frankia species genomic map is subcloned from the lambda-Dash vector to pUC19 for ease of manipulation in subsequent steps.

14. Sequencing: The DNA including and adjacent to the location of the 1650 bp amplification product is sequenced to determine the exact DNA sequence at the N-terminus of the endonuclease gene, including the four "missing" amino acid codons and the ATG start, and the sequence at the start of the methylase absent from the original amplification product. The second amino acid of the endonuclease was found to be different from the original sequence call (step 3). This amino acid is changed to the correct threonine in subsequent expression of the endonuclease. The putative start and stop of the methylase gene are identified, as is the end of the endonuclease. It is observed that the endonuclease and methylase genes overlap by 12 nucleotides.

15. Expression of the FseI methylase: The FseI methylase is cloned into the vector pSYX20, which is compatible with the vectors pAII17 and pRRS. Oligonucleatide primers designed to amplify the FseI methylase gene and facilitate its expression in the pSYX20 vector are synthesized, the methylase gene is amplified from Frankia species DNA, the amplified product is cleaved with the appropriate restriction enzymes and ligated into the pSYX20 vector previously cleaved with the same restriction endonucleases and transformed into ER2427 host cells. Individual transformants are picked and analyzed for the presence of the desired construct. One transformant with the S0 correct construct is named pRMFseM1.

16. Expression of the FseI endonuclease: DNA primers were designed to amplify the entire FseI endonuclease gene. The forward primer has the following elements: a BamHI cloning site, stop codon in frame with the lacZ gene, *E. coli* consensus strong ribosome binding site, 7 nucleotide spacer sequence between the ribosome binding site and the ATG start codon of the FseI endonuclease, a correct threonine codon at the second position, a change of the codon for leucine at the fifth position to an *E. coli* preferred codon and 24 nucleotides matching the FseI DNA sequence for hybridization. This primer follows the example of HinfI expression (Skoglund, et. al., *Gene* 88:1–5 (1990)). The 3' (reverse) primer is designed to hybridize just at the 3' end of the endonuclease gene, to minimize overlap with the methylase clone and thus the possibility of homologous recombination between the two plasmids in the host. A BamHI site is introduced in this primer to facilitate cloning. The endonuclease gene is amplified from the genomic Frankia species DNA. The amplified DNA is cleaved by BamHI and ligated into the expression vector pRRS, previously cleaved by BamHI and dephophorylated, and the ligation reaction is transformed into an appropriate host cell such as *E. coli* ER2427 pre-modified with the NlaI methylase carried on pSYX20. Vectors containing inserts of the desired size are identified by miniprep procedures. These clones are grown to mid-log phase and induced with 0.5 mM IPTG. The cells are then harvested by centrifugation, resuspended in sonication buffer and lysed by sonication. The extract is clarified and assayed for FseI endonuclease activity. The pRRS FseI endonuclease construct is named pRMFseR2. One FseI expressing host containing the plasmid pRMFseR2 is propagated and used to produce FseI restriction endonuclease.

17. Production: The FseI endonuclease may be produced from host cells carrying the overexpressed FseI restriction endonuclease gene and either the NlaI methylase gene or the FseI methylase gene by propagation in a fermenter in a rich medium with the appropriate antibiotic selection and induction. The cells are thereafter harvested by centrifugation and disrupted by sonication to produce a crude cell extract containing FseI restriction endonuclease activity.

18. Purification: The crude cell extract containing the FseI endonuclease is purified by a combination of standard protein purification techniques, such as affinity-chromatography or ion-exchange chromatography.

Although the above-outlined steps represent the preferred mode for practicing the present invention, it will be apparent to those skilled in the art that the above described approach can vary in accordance with techniques known in the art.

The following example is given to illustrate embodiments of the present invention as it is presently preferred to practice. It will be understood that this example is illustrative, and that the invention is not to be considered as restricted thereto except as indicated in the appended claims.

EXAMPLE 1

Cloning of FseI Modification Methylase and Restriction Endonuclease Genes

1. DNA purification: To prepare the DNA of Frankia species, 5 g of cell paste was resuspended by shaking gently for 10 min in 20 ml of 25% sucrose, 0.05 M Tris-HCl, 1 mM EDTA pH 8.0. 10 ml of 0.25M EDTA pH 8.0 and 6 ml of freshly prepared 10 mg/ml lysozyme in 0.25M Tris-HCl pH 8.0 was added and the solution was incubated at 4° C. for 16 hours. The solution was extracted with 50 ml of equilibrated phenol, the aqueous phase was recovered and extracted with 50 ml of chloroform two times. The DNA was precipitated by the addition of 1/10th volume 5M NaCl and 1 volume of 2-propanol and collected by centrifugation. The DNA pellet was air dried for 1 hour, then resuspended in 11 ml of DNA buffer (10 mM Tris-HCl, 1 mM EDTA pH 8.0). 10 g of CsCl was dissolved into the DNA solution and 0.5 ml of 5 mg/ml ethidium bromide solution added. The CsCl - DNA solution was centrifuged at 44,000 rpm for 36 hours in a Beckman Ti70 rotor. Following centrifugation the DNA band was pulled with a 17 gauge needle, extracted 4 times with CsCl-water-saturated 2-propanol, diluted with 4 volumes DNA buffer and precipitated with an equal volume of 2-propanol. The DNA was collected by centrifugation, washed twice with 70% ethanol, air dried and resuspended in 2 ml DNA buffer.

2. Purification of the FseI restriction endonuclease from Frankia species (NRRL 18528): FseI restriction enzyme may be produced from NRRL 18528 by propagation of Frankia species cells to mid-log phase in flasks containing rich broth. The cells are harvested by centrifugation. All of the following procedures were performed on ice or at 4° C. 25 g of cells were resuspended in 50 ml of buffer A (20 mM Tris-HCl, 1 mM Dithiothreitol (DTT), 0.1 mM EDTA, pH 7.6) and broken by sonication. The extract was brought to 0.2M NaCl by addition of 3 ml of 5M NaCl and centrifuged at 15,000 rpm for 30 minutes at 4° C. The supernatant was loaded onto a 15 ml heparin-sepharose column equilibrated with buffer A containing 0.2M NaCl (buffer A.2). The column was washed with 45 ml buffer A.2, followed by a linear gradient of NaCl formed with 60 ml buffer A.2 and 60 ml buffer A containing 1.0M NaCl 3 ml fractions were collected. The peak of restriction enzyme activity eluted from the column between 0.8 and 0.9M NaCl and was pooled. This heparin-sepharose pool was diluted with 3 volumes buffer A and applied to a 1 ml phosphocellulose column equilibrated in buffer A.2. The column was washed with 5 ml buffer A.2 and then a 40 ml linear gradient of 0.2M NaCl to 1.0M NaCl in buffer A was applied. The peak of restriction enzyme activity eluted at 0.5M NaCl and was pooled. The phosphocellulose pool was concentrated with an Amicon Centricon-10 microfiltration device to 0.56 ml and diluted with 5 ml of buffer A, then applied to a 1 ml Mono-Q® column (Pharmacia) equilibrated with buffer A supplemented to 0.05M NaCl. A linear gradient in buffer A from 0.05 to 0.6M NaCl was applied and the FseI activity eluted at 0.2M NaCl. The Mono-Q fraction containing the most pure FseI was concentrated with an Amicon centricon-10 device; however this resulted in the loss of greater than 90% of the soluble FseI activity. The filter membrane of the centricon-10 device was therefore boiled in 0.05 ml of SDS-protein-gel loading buffer, the supernatant was recovered and subjected to electrophoresis and electroblotted according to the procedure of Matsudaira (Matsudaira, P., J. Biol. Chem. 262:10035–10038, 1987), with modifications as previously described (Looney, et al., Gene 80:193–208, (1989)). The membrane was stained with Coomassie blue R-250, the protein band of approximately 28 kD was excised and subjected to sequential degradation (Waite-Rees et al., J. Bacteriol. 173:5207–5219, (1991)).

3. Amino terminal FseI protein sequence: The approximately 28 kD protein band obtained was subjected to amino terminal protein sequencing on an Applied Biosystems Model 470A gas phase protein sequencer (Brooks, et al., Nucleic Acids Research, 17: 979–997, (1989)). The sequence of the first 23 residues obtained was the following: H D E L F P I P E P L V X P V I A L P P L L K (SEQ ID NO:1). This peptide sequence data from the amino terminus of the FseI endonuclease was used to construct a series of PCR primers:

1) TTY CCN ATH CCN GAR CC 17 -mer, (SEQ ID NO:2)

2) GAG CTS TTC CCS ATC CCN GAR CC 23-mer, (SEQ ID NO:3)

3) CCS GTS ATC GCS CTS CCS CC 20-mer, (SEQ ID NO:4)

4) GGC TCS GGG ATS GGR AAN AGY TC 23-mer, (SEQ ID NO:5)

5) GGC TCS GGG ATS GGR AAY AAY TC 23-met, (SEQ ID NO: 6)

where

Y= T,C

R= A,G

H= A,T,C

S= G,C

N= A,C,G,T

Primers 1, 2 and 3 are forward, or coding strand primers, while 4 and 5 are reverse, or non-coding strand primers.

4. Primers to match cytosine methylase conserved sequences: The amino acid sequence of a number of cytosine methylase genes has been determined and compared (Wilson, Methods in Enzymology, 216:259–279, (1992)). There are two distinct types of cytosine methylation: one at the 5 position carbon (C5) of the cytosine ring and one at the 4 position nitrogen (N4). The N4 type occurs in two classes, alpha and beta, which have similar motifs that occur in different order. Degenerate DNA primers were designed to hybridize to several of the conserved sequence motifs of each type of cytosine methylase, with some priming in the forward (coding) direction and some in the reverse direction, as follows:

A. 5-methyl-cytosine:

5' TTC GCN GGN ATH GGN GG 3' (SEQ ID NO:7), motif I: FAGIGG (SEQ ID NO:37)

5' TTC TCN GGN GCN GGN GG 3' (SEQ ID NO:8), motif 1: FSGAGG (SEQ ID NO:38)

5' TTY TCN GGN TGY GGN GG 3' (SEQ ID NO:9), motif 1: FSGCGG (SEQ ID NO:39)

5' GCN GGN TTY CCN TGY CA 3' (SEQ ID NO:10), motif 4: AGFPCQ (SEQ ID NO:40)

5' GGS GGN CCN CCN TGY CA 3' (SEQ ID NO:11), motif 4: GGPPCQ (SEQ ID NO:41)

5' TG RCA NGG RAA NCC NGC 3' (SEQ ID NO:12), motif 4: AGFPCQ (SEQ ID NO:42)

5' TG RCA NGG NGG NCC 3' (SEQ ID NO:13), motif 4: GPPCQ (SEQ ID NO:43)

5' CC YTT NAC RTT YTC 3' (SEQ ID NO:14), motif 6: ENVKG (SEQ ID NO:44)

5' AR NCC YTT NAC RTT YTC 3' (SEQ ID NO:15), motif6: ENVKGX (X=leucine/phenylalanine (SEQ ID NO:45))

5' AC SGG SAC SGC GTT SCC 3' (SEQ ID NO:16), motif 10:GNAVPV (SEQ ID NO:46)

B. N-4 cytosine methylase, alpha type:

5' GGN TCN GGN AC 3' (SEQ ID NO:17), motif 1: GSGT (SEQ ID NO:47).

5' TA NGG NGG NGA 3' (SEQ ID NO:18), motif 4: SPPY (SEQ ID NO:48)

C. N-4 cytosine methylase, beta type:

5' ACN TCN CCN CCN TA 3' (SEQ ID NO:19), motif 4: TSPPY (SEQ ID NO:49)

5' ACN AGY CCN CCN TA 3' (SEQ ID NO:20), motif 4: TSPPY (SEQ ID NO:49)

5' TCN CCN CCN TAY TGG 3' (SEQ ID NO:21), motif 4: SPPYW (SEQ ID NO:50)

5' AA NGG RTC NAG NAC 3' (SEQ ID NO:22), motif 1: VLDPF (SEQ ID NO:51)

5' GT NGT NCC NGA NCC 3' (SEQ ID NO:23), motif 1: GSGTT (SEQ ID NO:52)

5' CC CAT RAA NGG RTC 3' (SEQ ID NO:24), motif 1: DPFMG (SEQ ID NO:53)

5' CC RAA RAA NGG RTC 3' (SEQ ID NO:25), motif 1: DPFFG (SEQ ID NO:54)

5' CC NGC RAA NGG RTC 3' (SEQ ID NO:26), motif 1: DPFAG (SEQ ID NO:55)

5. Various combinations of the cytosine methylase primers of section 4 and the primers complementary to the N-terminus region of the FseI endonuclease gene of section 3 were employed in polymerase chain reaction techniques to amplify a portion of the endonuclease and methylase genes. In a typical reaction a master reaction mix was made containing one primer being tested and divided into aliquots to which the second primer was added. In the reaction that was successful in amplifying a portion of the FseI methylase and endonuclease, a master reaction mix was made by combining:

40 ul 10X Vent™ reaction buffer 30 ul of 4 mM dNTP solution 4 ul (800 ng) Frankia species DNA 20 ul (10 uM stock) primer SEQ ID:2 above (FseI endonuclease N-terminus primer)

286 ul dH$_2$O 4 ul KlenTaq™ polymerase (25 unit/ul stock)

4 ul Deep Vent™ polymerase (0.02 unit/ul stock)

The mix was then split into eight 47.5 ul aliquots; to the first was added 2.5 ul primer SEQ ID NO:8 (10uM stock), to the second was added 2.5 ul primer SEQ ID NO:10 (10 uM stock) and so on using primers SEQ ID NO:8, SEQ ID NO:10, SEQ ID NO:11, SEQ ID NO:12, SEQ ID NO:13, SEQ ID NO:15 and SEQ ID NO:16. To the eighth aliquot was added 2.5 ul dH$_2$O as a control reaction. The PCR amplification conditions were 94° C. for 3 minutes for one cycle, followed by 25 cycles of 95° C. for 30 seconds, 46° C. for 30 seconds and 72° C. for 2 minutes. 15 ul of the PCR reaction product was analyzed by electrophoresis on a 1% agarose gel. Multiple bands were observed in the reactions with primers SEQ ID NO:8 and SEQ ID NO:16 with various second primers. A prominent band of approximately 1.5 kb was observed in the reaction with primers SEQ ID NO:2 and SEQ ID NO:11. A faint product of the same size was observed with primers SEQ ID NO:2 and SEQ ID NO:10, and a medium intensity band of approximately 1.65 kb was observed with primers SEQ ID NO:2 and SEQ ID NO:8. These size products are consistant with expectations for a convergent gene orientation.

As a test of whether these products were derived from the FseI methylase and endonuclease, the 1.65 kb product of primers SEQ ID NO:2 and SEQ ID NO:8 was gel purified and used as a PCR template. Gel purification: 30 ul of the SEQ ID NO:2 to SEQ ID NO:8 PCR reaction was electrophoresed into 1% LMP agarose, the 1.65 kb band was excised from the gel, melted at 65° C. for five minutes, cooled to 40° C. for 5 minutes and the agarose was digested by the addition of 1 ul (1 u) β-agarase (New England Biolabs #392) with incubation at 40° C. for 1 hour. The DNA was recovered by precipitation, washed with 70% ethanol, air dried and resuspended in DNA buffer. PCR reactions were performed using conditions as above with the following primer combinations: SEQ ID NO:8 alone gave 6 faint bands of sizes different from 1.65 kb, primer SEQ ID NO:2 alone gave no product, primers SEQ ID NO:2 plus SEQ ID NO:8 produced a prominent 1.65 kb band, primers SEQ ID NO:2 plus SEQ ID NO:11 (an internal 5-methyl cytosine methylase primer) produced a prominent 1.5 kb band, as these had from Frankia species DNA, and primers SEQ ID NO:4 (an internal FseI endonuclease N-terminus primer) plus SEQ ID NO:11 produced a prominent band of approximately 1.45 kb. These results indicated the 1.65 kb product and the 0 1.5 kb product originally obtained were very likely derived from the FseI endonuclease and methylase genes. Both the 1.65 kb and 1.5 kb products were gel purified as above, kinased with T4 Polynucleotide Kinase and ligated into pUC19 vector previously cleaved with SmaI and dephosphorylated with Calf Intestinal Alkaline Phosphatase. The ligation mixture was then transformed into E. coli strain ER2420 and plated on L-broth plates containing 100 ug/ml ampicillin for individual colonies. Clones of the desired construct were identified by performing minipreps, digesting the purified DNA and analyzing it by agarose gel electrophoresis.

Analysis of plasmid clones: Individual transformants were innoculated into 10 ml cultures of L-broth containing ampicillin and the plasmids that they carried were prepared by the following miniprep plasmid purification procedure, adapted from the method of Birnboin and Doly (Nucleic Acids Res. 7:1513, (1979)).

Miniprep Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2 M NaOH, 1% SDS was added to each tube and the tubes were shaken to lyse the cells and then placed on ice. Once the solutions had cleared, 1.5 ml of 3 M sodium acetate pH 4.8, was added to each and shaken. The precipitates that formed were spun down at 15,000 rpm, 4° C. for 10 minutes. Each supernatant was poured into a centrifuge tube containing 3 ml of isopropanol and mixed. After 10 minutes at room temperature, the tubes were spun at 15,000 rpm for 10 minutes to pellet the precipitated nucleic acids. The supernatants were discarded and the pellets were air-dried at room 30 temperature for 30 minutes. Once dry, the pellets were dissolved in 500 ul of 10 mM Tris pH 8.0, 1 mM EDTA, containing 50 ug/ml RNase and incubated for 1 hour at 37° C. to digest the RNA. The DNA was precipitated by the addition of 50 ul of 5 M NaCl followed by 350 ul of 35 isopropanol. After 10 minutes at room temperature, the DNA was spun down by centrifugation for 5 minutes, the supernatants were discarded, the pellets were dried and then redissolved in a final solution of 150 ul of 10 mM Tris, 1 mM EDTA pH 8.0. The plasmid minipreps were subsequently analyzed by digestion with various restriction endonucleases.

6. DNA Sequencing: DNA sequencing was performed using the Circumvent™ DNA sequencing kit (New England Biolabs) according to the manufacturers instructions. Miniprep DNA preparations were used as templates. The DNA sequence provided data to use as a basis for subsequent manipulations to clone the entire restriction endonuclease gene and to induce expression of the cloned gene in *E. coli*. The amino acid sequence deduced from the DNA sequence at one end of both the 1.65 kb and 1.5 kb PCR products closely matched the protein sequence of the N-terminus of the FseI endonuclease gene. This DNA sequence was found to be: 5' TTT CCT ATT CCG GAG CCA TTG GTC AGA CCA GTC ATC GCA CTC CCC CCT CAT CTG AAG GAA TTG ATC 3' (SEQ ID N0:27), which translates into the amino acid sequence: F P I P E P L V R P V I A L P P H L K E L I (SEQ ID NO:28), where the amino acids in bold match the N-terminus amino acid sequencing data interpretation from the FseI endonuclease. Amino acid sequence deduced from the DNA sequence at the other end of the 1.65 kb amplification product contained conserved motifs 1 and 4 of 5-methyl cytosine methylases: DNA sequence 5' TTC TGT GGC GCC GGA GGG ATG ACG TTG GGA TTC ATG CAG GCA GGA TTC CAG CCG ATT CTG TCC ATC GAC CAT GAC S0 CTT CCA TCT ATCGAG ACG CAT CGC GCA AAC TTC CCT GGA ATG TCG ATC TGC ACG GAC ATT CGC GAC TTT GTT GAT TTT CCT TCC GCA GAT GTT GTC GTC GGA GGT CCC CCA TGC CAG GGA TTC AGT CGT CTG GGT 3' (SEQ ID N0:29), which translates into the amino acid sequence: F C G A G G M T L G F M Q A G F Q P S5 ILSIDHDLPSIETHRANFPGM- SICTDIR D F V D F P S A D V V V G G P C Q G F S R L G (SEQ ID N0:30) .

Figure 4:
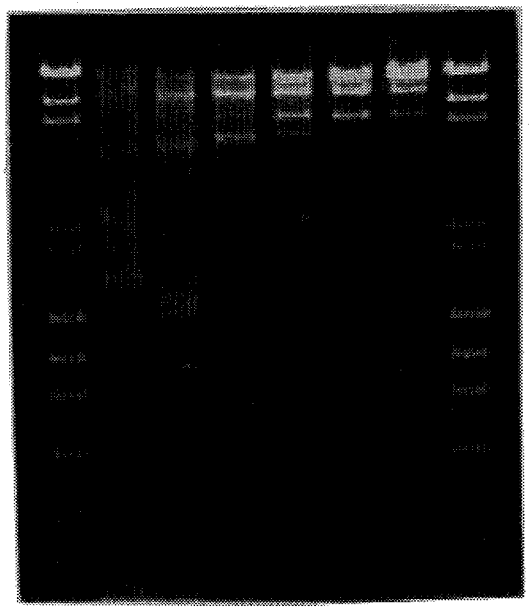
FIG. 4 is a photograph of an agarose gel demonstrating FseI restriction endonuclease activity in cell extracts of *E. coli* ER2417 carrying the endonuclease on the pAII17 derived plasmid pRMFseR1.

7. Overexpression of the FseI endonuclease: The FseI endonuclease gene was overexpressed by inserting the gene into an expression vector, pAII17, directly downstream of an inducible promoter (T7) and strongly recognized ribosome binding site. To accomplish this, two oligonucleotide primers were made using the DNA and protein sequence data. The forward oligonucleotide primer contained sequence to create an NdeI cloning site at an ATG start codon for the endonuclease, followed by DNA sequence to code for the second, third, fourth and fifth amino acids indicated by protein sequencing, with the choice of codons made to match the most common *E. coli* codon usage of highly expressed genes, followed by 21 bases complementary to the DNA sequence obtained from the 1.65 kb amplification product: 5' GGA GGT TAA CAT ATG CAC GAC GAA CTG TTT CCT ATT CCG GAG CCA TTG 3' (SEQ ID NO:31), with the NdeI cloning site in bold and the first five amino acid codons underlined. The second oligonucleotide primer contains sequence approximately 800 nucleotides 3' to the end of the FseI endonuclease gene, with one nucleotide changed to create a SalI site to aid the cloning of the fragment once amplified: 5' GAT GTT GTC GAC GGA GGT CCC CCA TGC 3' (SEQ ID N0:32), (SalI site in bold). These two primers were used with genomic Frankia species DNA as the template in PCR reactions using Vent™ DNA polymerase to amplify a 1.5 kb DNA fragment containing the FseI endonuclease gene. The band was gel purified as above. The purified DNA was digested with 20 U of NdeI and 20 U SalI in 1X NEBuffer 3 for 1 hr. After incubation the digest was extracted once with a 1: 1 mixture of phenol: chloroform, 35 twice with chloroform, and precipitated with 2 volumes of ethanol. The DNA was pelleted by centrifugation, washed once in 70% ethanol, dried and resuspended in 20 µl TE. 3 ul of the purified fragment (~0.05 ug) was ligated into the T7 expression vector, pAII17 (from S. Xu, New England Biolabs), which had been digested with NdeI and SalI (~0.05 ug) in a total volume of 20 ul with 400 U of T4 DNA ligase at 17° C. for 4 hours. [pAII17 is a T7 expression vector derived from pBR322 that contains a lac operator 4 bp down stream of the T7 promotor (called T71ac), the lacIq gene, ampicillin resistance, and two restriction sites for cloning, NdeI and SalI (SalI replacing BamHI). pAII17 also contains four copies of rrnB transcription terminator upstream of the T7 promotor to further decrease the basal level of expression of the target gene. (paII17 constructed at New England Biolabs by W. Jack) from pET-11a (Dubendorff, J. W. and Studier, F. W., J. Mol. Biol. 219:45–59, (1991)). 10 ul of the ligation was used to transform competent *E. coli* ER2417 pre-modified with the NlaI methylase gene carled on the compatible plasmid pNlaIH14. [The NlaI methylation recognition site, GGCC, occurs twice in every FseI restriction endonuclease recognition site and so methylation by NlaI protects the host DNA from FseI digestion. pNlaIH14 is derived from pSYX20, a medium copy number plasmid that carries kan$^r$ and Tc$^r$ genes and a pSC101 replication origin. A methylase gene inserted into the Tc$^r$ gene can be expressed constitutively from the Tc promoter. ] The transformed cells were plated on L-agar with ampicillin (100 µg/ml) and kanamycin (50 ug/ml). Plasmids were SO isolated from individual colonies, using the mini plasmid prep procedure as described in step 5. NdeI and SalI double digests of 5 µl of each miniprep were compared with NdeI and SalI double digests of pAII17. Clones containing an insert of approximately 1.5 kb were chosen for further characterization. These clones were grown in 200 ml L-broth with ampicillin and kanamycin to a Klett of 80 (mid log phase) and induced with 0.5 mM IPTG. At 2 hours after induction the cells (approximately 0.8 g) were harvested by centrifugation, resuspended in 3 ml of Sonication buffer (20 mM Tris-HCl pH 7.5, 1 mM DTT, 0.1 mM EDTA), and sonicated on ice. The sonicated cell extract was centrifuged at 16,000 rpm for 20 minutes. 4.5 ul of each extract was mixed with 5 ul of a DNA assay mixture (containing 1 ug Adeno2 DNA per 50 ul in NEBuffer 1). 25 ul from this tube was mixed with 50 ul of the DNA mixture in a second tube, a 2 dilution. 3 other successive 1:2 dilutions were performed. The reactions were incubated at 30° C. for 1 hour. 20 ul of each reaction was run on a 1% agarose gel. All clones tested produced FseI restriction endonuclease activity. It was estimated that the enzyme titer was greater than 1×10$^4$ units/g of cells. One of these clones was selected for further characterization and was given a strain designation of NEB# 918, with the plasmid named pRMFseR1. A titration of the FseI restriction endonuclease activity produced from crude extracts of NEB# 918 is shown in FIG. 4.

8. Production: The FseI restriction endonuclease may be produced from NEB# 918 by propagation to late-log phase in a fermenter containing rich medium with ampicillin (100 ug/ml) and kanamycin (50 ug/ml). The culture is then induced by the addition of IPTG to a final concentration of 0.5 mM and allowed to continue growing for 2 to 4 hours. The cells are then harvested 30 by centrifugation.

9. Purification of the FseI restriction endonuclease from NEB# 918: The crude cell extract containing the FseI endonuclease was purified by a 35 combination of standard protein purification techniques, such as affinity-chromatography or ion-exchange chromatography, as in step 2 above. The FseI restriction endonuclease obtained from this purification was substantially pure and free of non-specific endonuclease and exonuclease.

Further characterization of the FseI endonuclease and cloning of the FseI methylase:

10. Restriction endonuclease cleavage of Frankia species genomic DNA: Frankia species DNA was cleaved with Sau3AI to achieve partial digestion as follows: 450 ul of Frankia species DNA at 50ug/ml in NEBuffer Sau3AI (100 mM NaCl, 10 mM Bis Tris Propane-HC1, 10 mM $MgCl_2$, 1 mM DTT, pH 7.0 at 25° C.) was divided into one 100 ul aliquot and seven, 50 ul aliquots. To the 100 ul tube was added 5 units of Sau3AI to achieve 1 unit of enzyme per ug of DNA. 50 ul was withdrawn from the first tube and transferred to the second tube to achieve 0.5 units Sau3AI/ug, and so on, each succeeding tube receiving half of the previous amount of Sau3AI. The tubes were incubated at 37° C. for one hour, then phenol/chloroform extracted, precipitated with 2 volumes ethanol, dried and resuspended in 30 ul TE (TE=10 mM Tris-HC1, 1 mM EDTA, pH 8.0) and 3 ul from each was analyzed by agarose gel electrophoresis. Tubes exhibiting digestion products in the 9 to 23 kb range were chosen as the source of fragments for cloning. The separate reactions were mixed together and fragments of the desired 9 to 23 kb range were gel purified from low 30 melt agarose, as described above, and used to form a library of clones.

11. Sau3AI library: A Sau3AI genomic library was constructed using the vector lambdaDash™ II (Stratagene). Lambda Dash™ II is lambda substitution vector that can be used to clone DNA fragments of 9–23 kb. 250 ng (2 ul) of Sau3AI partially digested Frankia species DNA, as described above, was mixed with 500 ng of BamHI-cleaved lambda Dash™ II arms (0.5 ul). 2.5 ul of 2X ligation mix (100 mM Tris pH 7.8, 20 mM $MgCl_2$, 20 mM DTT, 2 mM ATP) containing 1000 units T4 DNA ligase was added and the mixture incubated at 17° C. for 16 hours. 2.5 ul of the ligation reaction was packaged in vitro into infective phage particles using Gigapack® II Plus (Stratagene) according to the manufacturers instructions. Following incubation at room temperature for two hours, the packaged phage were diluted in 500 ul of SM (SM= 100 mM NaCl, 8 mM $MgSO_4$, 50 mM Tris-HCl pH 7.5, 0.01% gelatin) plus three drops of chloroform. The titer of infective phage particles was determined as follows. 2 ul of the packaged phage solution was diluted into 198 ul SM. 1 ul, 10 ul and 100 ul aliquots of the diluted phage was added to 100 ul of a fresh suspension of ER1458 cells (in 10 mM Tris-HCl pH 7.5, 10 mM $MgCl_2$, O.D.600=2.0), incubated at RT for 15 minutes, then mixed with 3 ml top agar at 40° C. and spread on rich plates. After the top agar hardened the plates were incubated at 37° C. overnight. The plaques were counted the next day and the titer of the phage stock used in subsequent experiments was calculated to be $5 \times 10^4$ pfu/ml.

12. The in vitro packaged phage were plated, as above, to form well separated plaques in lawns of *E. coli* ER1458. Plates of approximately 250, 500, and 1500 phage were made. Nitrocellulose filter plaque lifts of these clones from the lambda Dash™ Sau3AI library were probed with radiolabeled (Random Priming System I, #1550, New England Biolabs) gel purified 1.65 kb PCR product (Benton-Davis method, In: *Molecular Cloning, a Laboratory Manual* by T. Maniatis, E. F. Fritsch and J. Sambrook, Cold Spring Harbor Laboratory Press, 1982, pp. 320ff). 6 positive plaques were identified and all were plaque purified. DNA was prepared from confluent plate lysates (in top agarose) of 4 phage and digested with SacI, KpnI and SalI. All four contained a common 1.8 kb KpnI fragment, to which 1.65 kb probe hybridized.

13. Southern hybridization: A Southern blot was prepared as follows: 1 ug of Frankia species genomic DNA was digested with ApaI, AscI, BamHI, EagI, HindIII, KpnI, MscI, NotI, PstI, SacI, SalI, SmaI, SphI, StuI, XbaI or XhoI. The digests were electrophoresed on a 0.7% agarose gel. The gel was washed in two changes of 0.25 M HCl for 15 minutes, then in two changes of 0.5M NaOH, 1.5 M NaCl for 15 minutes each and finally in two changes of 1M NH4OAc, 0.02 M NaOH for 30 minutes. To transfer the DNA to nitrocellulose, a sheet of 0.45 um pore size nitrocellulose was wet in 1M NH4OAc, 0.02 M NaOH and a piece the same size as the gel was placed on either side of the gel. This was placed on top of a two inch high stack of paper towels and another two inch stack of paper towels was placed on top. A glass plate was placed on the top of the stack and a small weight was placed on the plate. The DNA transfer was allowed to proceed overnight. The nitrocellulose was dried and baked at 80° C. for one hour.

The nitrocellulose blot was pre-hybridized in 15 mls of 50X Denhardt's (5 g ficoll, 5g polyvinylpyrrolidone, 5g BSA in 500 mls $H_2$), 20×SSC (175.3 g NaCl, 88.2 g Sodium citrate in 1L $H_2$), 10% SDS and 10% dextran sulfate. After prehybridizing at room temperature for one hour, the labelled probe (1.65 kb amplification product, labeled as above) was added and the hybridization step was carried out at 68° C. S5 overnight. The blot was washed in three changes of 2×SSC and three changes of 2×SSC with 0.1% SDS over the period of one hour at 65° C. The blot was exposed to X-ray film for 24 hours.

From this blot and the digestion pattern of the lambda clones, a 3.6 kb SacI fragment containing the entire FseI endonuclease and a portion of the carboxyl-terminal end of the FseI methylase gene was identified and subcloned from one of the lambda phage into pUC19. A 7.0 kb KpnI fragment containing the entire FseI methylase gene and the carboxyl-terminal end of the FseI endonuclease gene was also subcloned into pUC19, as was a 1.8 kb KpnI fragment containing the remaining amino-terminal portion of the FseI endonuclease gene.

14. DNA Sequencing: DNA sequencing of the FseI endonuclease and methylase genes was performed using the Circumvent™ DNA sequencing kit (New England Biolabs) and Sequenase™ 2.0 sequencing kit (United States Biochemicals) according to the manufacturers instructions. Various subclones were made and synthetic oligonucleotide primers were synthesized to accomplish the sequencing. Miniprep DNA preparations were used as templates. The DNA sequence provided data to use as a basis for subsequent manipulations to clone the FseI methylase gene and to reclone the FseI endonuclease gene and to induce expression of these genes in *E. coli*. The DNA sequence at the start of the endonuclease was found to be 5' TG ACC GAC GAG TTG TTT CCT ATC CCG GAG CCA TTG GTC 3' (SEQ ID N0:33). This translates into the amino 30 acid sequence M T D E L F P I P E P L V (SEQ ID N0:34). The second amino acid of the endonuclease was thus found to be threonine, not histidine as originally thought from the amino acid sequencing data of step 3. The putative start and stop of the methylase gene were 35 identified, as was a stop codon presumed to be the end of the endonuclease. It was observed that the open reading frames of the endonuclease and methylase genes overlap by 12 nucleotides. The FseI methylase was expressed in a compatible vector to use FseI methylase for protection of the host genome from FseI cleavage, and a second expression of the endonuclease was made to incorporate the canonical threonine at the second position and use the FseI methylase for protection.

15. Methylase cloning: Two primers were designed to amplify the FseI methylase gene for cloning into pSYX20. The FseI methylase gene was amplified from Frankia species genomic DNA using Vent™ DNA polymerase. The amplification product of approximately 1100 bp was gel purified as above, cleaved with BamHI and SalI, phenol-chloroform extracted, precipitated and ligated into pSYX20 vector previously cleaved with BamHI and SalI. The ligation reaction was transformed into *E. coli* strain ER2427 and individual transformants were miniprepped and digested with BamHI and SalI. Transformants with the correct insert were isolated.

Figure 5:
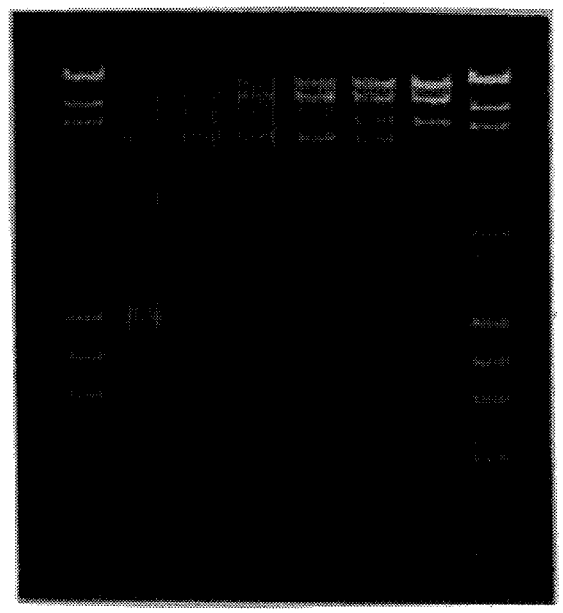
FIG. 5 is a photograph of an agarose gel demonstrating FseI restriction endonuclease activity in cell extracts of *E. coli* ER2427 carrying the endonuclease on the pRRS derived plasmid pRMFseR2.

16. Endonuclease cloning: The restriction endonuclease gene was expressed by inserting the gene into an expression vector, pRRS, directly downstream of a strong inducible promotor (PlacUV5) and strongly recognized ribosome binding site. To accomplish this, two oligonucleotide primers were made using the DNA and protein sequence data. The first oligonucleotide primer contained a BamHI site followed by a stop codon in frame with the lacZ gene to terminate translation of the lacZ protein, then a strong ribosome binding site, seven nucleotide spacer, the start of the FseI endonuclease gene, a threonine codon rather than histidine at position 2, a change in codon usage for leucine at amino acid 5 and sequence complementary to Frankia species DNA for hybridization: 5' TAG GAT CCG GAG GTT TAAAAT ATG ACC GAC GAG CTG TTT CCT ATC C 3' (SEQ ID N0:35). The reverse primer was located at the 3' end of the endonuclease gene and had a BamHI site added for cloning: 5'TAA GGA TCC TCT AGA GCA GGT CGG 3' (SEQ ID NO:36). These two primers were used to amplify the FseI endonuclease gene from Frankia species genomic DNA by combining:

10 ul 10X Vent™ reaction buffer
8 ul of 4 mM dNTP solution
1 ul (200 ng) Frankia species DNA
5 ul (10uM stock) primer (SEQ ID NO:35)
5 ul (10uM stock) primer (SEQ ID N0:36)
71 ul dH$_2$O
0.5 ul Vent™ polymerase (2 unit/ul stock)

and amplifying at 95° C. for 1 minute, 56° C. for 1 minute and 72° C. for 1 minute for 25 cycles. The amplification product of approximately 700 bp was gel purified as above, cleaved with BamHI, phenol-chloroform extracted, precipitated and ligated into pRRS vector previously cleaved with BamHI and dephosphorylated. The ligation reaction was transformed into *E. coli* strain ER2427 previously modified with the NlaI methylase gene carried on the compatible plasmid pSYX20. Individual transformants were analyzed and several expressing FseI endonuclease were found. It was estimated that the enzyme titer was greater than $1 \times 10^4$ units/g of cells. One of these clones was selected for further characterization and was given a strain designation of NEB# 943, with the plasmid named pRMFseR2. A sample of NEB# 943 was deposited at The American Type Culture Collection at Rockville, Maryland on Oct. 18, 1994 Accession No. 69707. A titration of the FseI restriction endonuclease activity produced from crude extracts of NEB# 943 is shown in FIG. 5.

17. The FseI restriction endonuclease may be produced from NEB# 943 by propagation to late-log phase in a fermenter containing rich medium with ampicillin (100 ug/ml), kanamycin (50 ug/ml) and chloramphenicol (15 ug/ml). The culture is then induced by the addition of IPTG to a final concentration of 0.5 mM and allowed to continue growing for 2 to 4 hours. The cells are then harvested by centrifugation.

18. Purification of the FseI restriction endonuclease from NEB# 943 is accomplished as for NEB#918 in section 9 above. The FseI restriction endonuclease obtained from this purification was substantially pure and free of non-specific endonuclease and exonuclease.

What is claimed is:

1. Isolated DNA coding for FseI restriction endonuclease, wherein the isolated DNA is obtainable from the plasmid pRMFseR2.

2. A recombinant vector comprising a vector into which DNA coding for FseI restriction endonuclease has been inserted.

3. A recombinant vector comprising the isolated DNA of claim 1.

4. The recombinant vector of claim 3, wherein the vector comprises the plasmid pRMFseR2.

5. A host cell transformed with the recombinant vector of claim 2, 3 or 4.

6. A method of producing FseI restriction endonuclease comprising culturing a host cell transformed with the vector of claim 2, 3 or 4 under conditions suitable for expression of said endonuclease.

7. The isolated DNA of claim 1, wherein the isolated DNA comprises SEQ ID N0:27.

8. A method for cloning restriction endonuclease and the corresponding methylase genes comprising employing degenerate primers based on conserved amino acid sequences of methylase genes with degenerate DNA primers based on partial protein sequence data of the endonuclease to amplify a portion of both genes, and using this amplification product to clone the entire endonuclease and methylase genes.

* * * * *

UNITED STATES PATENT AND TRADEMARK OFFICE
CERTIFICATE OF CORRECTION

PATENT NO. : 5,543,308  Page 1 of 5

DATED : August 6, 1996

INVENTOR(S) : Morgan.

It is certified that error appears in the above-indentified patent and that said Letters Patent is hereby corrected as shown below:

Column 2, line 59, replace "restictive" with --restrictive--

Column 3, line 1, replace "abscence" with --absence--

Column 4, line 41, replace "FIG. 1" with --FIG 1A and 1B--

Column 7, line 15, replace "FIG. 1" with --FIG 1A and 1B--

Column 9, line 42, replace "infect ire" with --infective--

Column 10, line 14, replace "Oligonucleatide" with --Oligonucleotide--

Column 10, line 43, replace "dephophorylated" with --dephosphorylated--

Column 11, line 54, replace "NaCl 3" with --NaCl. 3--

Column 12, line 9, replace "10038, 1987)" with --10038 (1987))--

Column 13, line 10, replace "motif6" with --motif 6--

Column 16, line 20, replace "pall17" with --pAll17--

Column 16, line 24, replace "carled" with --carried--

UNITED STATES PATENT AND TRADEMARK OFFICE
CERTIFICATE OF CORRECTION

PATENT NO. : 5,543,308

DATED : August 6, 1996

INVENTOR(S) : Morgan.

It is certified that error appears in the above-indentified patent and that said Letters Patent is hereby corrected as shown below:

Column 4, line 19, delete "S5"

Column 4, line 55, after "pRMFseR1" insert
--Lanes 1 and 8: *Hind*III-lambda + *Hae*III-PhiX174 size standard, lane 2: 3 ul crude extract per 50 ul reaction volume, lane 3: 1 ul crude extrace, lane 4: 0.3 ul crude extract, lane 5: 0.1 ul crude extract, lane 6: 0.03 ul crude extract, lane 7: 0.01 ul crude extract. Reaction condition: 1 ug Adeno2 DNA per 50 ul reaction volume in 1X NEBuffer 2, incubation at 30°C for one hour.--

Column 4, line 59, after "pRMFseR2" insert
--Lanes 1 and 8: *Hind*III-lambda + *Hae*III-PhiX174 size standard, lane 2: 3 ul crude extract per 50 ul reaction volume, lane 3: 1 ul crude extract, lane 4: 0.3 ul crude extract, lane 5: 0.1 ul crude extract, lane 6: 0.03 ul crude extract, lane 7: 0.01 ul crude extract. Reaction conditions: 1 ug Adeno2 DNA per 50 ul reaction volume in 1X NEBuffer 2, incubation at 30°C for one hour.--

Column 6, lines 4-5, replace "methylares" with --methylates--

Column 7, line 36, delete "S0".

Column 8, line 5, delete "S5"

Column 8, line 33, delete "S0"

UNITED STATES PATENT AND TRADEMARK OFFICE
CERTIFICATE OF CORRECTION

PATENT NO. : 5,543,308                           Page 3 of 5

DATED : August 6, 1996

INVENTOR(S) : Morgan.

It is certified that error appears in the above-indentified patent and that said Letters Patent is hereby corrected as shown below:

Column 10, line 22, delete "S0"

Column 12, line 35, replace "23-met" with --23-mer--

Column 14, line 33, replace "0 1.5 kb" with --1.5 kb--

Column 14, line 66, delete "30"

Column 15, line 3, delete "35"

Column 15, lines 25-26, replace "F P I P E P L V R P V I A L P P H L K E L I" with --F P E P E P L V R P V I A L P P H L K E L I--

Column 15, line 34, delete "S0"

Column 15, line 40, delete "S5"

Column 15, lines 57-58, replace "CAT ATG CAC GAC GAA CTG" with --CAT <u>ATG CAC GAC GAA CTG</u>--

Column 15, line 64, replace "GTC GAC" with --GTC GAC--

Column 16, line 5, delete "35"

Column 16, line 34, delete "30"

Column 16, line 38, delete "35"

UNITED STATES PATENT AND TRADEMARK OFFICE
CERTIFICATE OF CORRECTION

PATENT NO. : 5,543,308

DATED : August 6, 1996

INVENTOR(S) : Morgan.

It is certified that error appears in the above-indentified patent and that said Letters Patent is hereby corrected as shown below:

Column 16, line 47, replace "5" with --75--

Column 16, line 50, replace "2 dilution" with --1:2 dilution--

Column 16, last line, delete "30"

Column 17, line 3, delete "35"

Column 17, line 30, delete "30"

Column 17, line 54, replace "O.D.600" with --O.D.$_{600}$--

Column 18, line 16, replace "NH4OAc" with --NH$_4$OAc--

Column 18, line 18, replace "NH4OAc" with --NH$_4$OAc--

Column 18, line 28, replace "H2" with --H$_2$O--
   (Application, page 37, line 29)

Column 18, line 29, replace "H2" with --H$_2$O--

Column 18, line 33, delete "S5"

Column 18, line 59, replace "5' TG" with --5' ATG--

Column 18, line 61, delete "30"

Column 18, line 66, delete "35"

UNITED STATES PATENT AND TRADEMARK OFFICE
CERTIFICATE OF CORRECTION

PATENT NO. : 5,543,308

DATED : August 6, 1996

INVENTOR(S) : Morgan.

It is certified that error appears in the above-indentified patent and that said Letters Patent is hereby corrected as shown below:

Column 42, line 55, delete "genes"

Column 42, line 57, replace "genes" with --gene--

Signed and Sealed this

Eleventh Day of February, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 55

( 2 ) INFORMATION FOR SEQ ID NO:1:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:1:

```
His  Asp  Glu  Leu  Phe  Pro  Ile  Pro  Glu  Pro  Leu  Val  Xaa  Pro  Val  Ile
 1              5                        10                       15
Ala  Leu  Pro  Pro  Leu  Leu  Lys
               20
```

( 2 ) INFORMATION FOR SEQ ID NO:2:

( i ) SEQUENCE CHARACTERISTICS:

( A ) LENGTH: 17 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:2:

TTYCCNATHC CNGARCC    17

( 2 ) INFORMATION FOR SEQ ID NO:3:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:3:

GAGCTSTTCC CSATCCCNGA RCC    23

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:4:

CCSGTSATCG CSCTSCCSCC    20

( 2 ) INFORMATION FOR SEQ ID NO:5:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:5:

GGCTCSGGGA TSGGRAANAG YTC    23

( 2 ) INFORMATION FOR SEQ ID NO:6:

( i ) SEQUENCE CHARACTERISTICS:
( A ) LENGTH: 23 base pairs
( B ) TYPE: nucleic acid
( C ) STRANDEDNESS: unknown
( D ) TOPOLOGY: unknown ( i i ) MOLECULE TYPE: protein ( x i ) SEQUENCE DESCRIPTION: SEQ ID NO:6:

GGCTCSGGGA TSGGRAAYAA YTC    23

( 2 ) INFORMATION FOR SEQ ID NO:7:

( i ) SEQUENCE CHARACTERISTICS:
( A ) LENGTH: 17 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:7:

TTCGCNGGNA THGGNGG 17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:8:

TTCTCNGGNG CNGGNGG 17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:9:

TTYTCNGGNT GYGGNGG 17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:10:

GCNGGNTTYC CNTGYCA 17

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

GGSGGNCCNC CNTGYCA 17

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

TGRCANGGRA ANCCNGC 17

( 2 ) INFORMATION FOR SEQ ID NO:13:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

TGRCANGGNG GNCC 14

( 2 ) INFORMATION FOR SEQ ID NO:14:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

CCYTTNACRT TYTC 14

( 2 ) INFORMATION FOR SEQ ID NO:15:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

ARNCCYTTNA CRTTYTC 17

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:16:

ACSGGSACSG CGTTSCC 17

( 2 ) INFORMATION FOR SEQ ID NO:17:

( i ) SEQUENCE CHARACTERISTICS:
        ( A ) LENGTH: 11 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

GGNTCNGGNA C 11

( 2 ) INFORMATION FOR SEQ ID NO:18:

( i ) SEQUENCE CHARACTERISTICS:

(A) LENGTH: 11 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:18:

TANGGNGGNG A  11

(2) INFORMATION FOR SEQ ID NO:19:

(i) SEQUENCE CHARACTERISTICS:
(A) LENGTH: 14 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:19:

ACNTCNCCNC CNTA  14

(2) INFORMATION FOR SEQ ID NO:20:

(i) SEQUENCE CHARACTERISTICS:
(A) LENGTH: 14 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:20:

ACNAGYCCNC CNTA  14

(2) INFORMATION FOR SEQ ID NO:21:

(i) SEQUENCE CHARACTERISTICS:
(A) LENGTH: 15 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:21:

TCNCCNCCNT AYTGG  15

(2) INFORMATION FOR SEQ ID NO:22:

(i) SEQUENCE CHARACTERISTICS:
(A) LENGTH: 14 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:22:

AANGGRTCNA GNAC  14

(2) INFORMATION FOR SEQ ID NO:23:

(i) SEQUENCE CHARACTERISTICS:
(A) LENGTH: 14 base pairs
(B) TYPE: nucleic acid
(C) STRANDEDNESS: unknown
(D) TOPOLOGY: unknown (  i  i  ) MOLECULE TYPE: DNA (genomic)

(  x  i  ) SEQUENCE DESCRIPTION: SEQ ID NO:23:

GTNGTNCCNG ANCC 14

( 2 ) INFORMATION FOR SEQ ID NO:24:

(  i  ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:24:

CCCATRAANG GRTC 14

( 2 ) INFORMATION FOR SEQ ID NO:25:

(  i  ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:25:

CCRAARAANG GRTC 14

( 2 ) INFORMATION FOR SEQ ID NO:26:

(  i  ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:26:

CCNGCRAANG GRTC 14

( 2 ) INFORMATION FOR SEQ ID NO:27:

(  i  ) SEQUENCE CHARACTERISTICS:
        ( A ) LENGTH: 66 base pairs
        ( B ) TYPE: nucleic acid
        ( C ) STRANDEDNESS: unknown
        ( D ) TOPOLOGY: unknown (  i  i  ) MOLECULE TYPE: DNA (genomic)

(  x  i  ) SEQUENCE DESCRIPTION: SEQ ID NO:27:

TTTCCTATTC CGGAGCCATT GGTCAGACCA GTCATCGCAC TCCCCCCTCA TCTGAAGGAA 60

TTGATC 66

( 2 ) INFORMATION FOR SEQ ID NO:28:

(  i  ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown (  i  i  ) MOLECULE TYPE: protein (  x  i  ) SEQUENCE DESCRIPTION: SEQ ID NO:28:

```
        Phe   Pro   Ile   Pro   Glu   Pro   Leu   Val   Arg   Pro   Val   Ile   Ala   Leu   Pro   Pro
        1                 5                             10                            15

His   Leu   Lys   Glu   Leu   Ile
                                20
```

( 2 ) INFORMATION FOR SEQ ID NO:29:

( i ) SEQUENCE CHARACTERISTICS:
        ( A ) LENGTH: 210 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:29:

```
TTCTGTGGCG   CCGGAGGGAT   GACGTTGGGA   TTCATGCAGG   CAGGATTCCA   GCCGATTCTG      60

TCCATCGACC   ATGACCTTCC   ATCTATCGAG   ACGCATCGCG   CAAACTTCCC   TGGAATGTCG     120

ATCTGCACGG   ACATTCGCGA   CTTTGTTGAT   TTTCCTTCCG   CAGATGTTGT   CGTCGGAGGT     180

CCCCCATGCC   AGGGATTCAG   TCGTCTGGGT                                           210
```

( 2 ) INFORMATION FOR SEQ ID NO:30:

( i ) SEQUENCE CHARACTERISTICS:
        ( A ) LENGTH: 70 amino acids
        ( B ) TYPE: amino acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:30:

```
        Phe   Cys   Gly   Ala   Gly   Gly   Met   Thr   Leu   Gly   Phe   Met   Gln   Ala   Gly   Phe
        1                 5                             10                            15

Gln   Pro   Ile   Leu   Ser   Ile   Asp   His   Asp   Leu   Pro   Ser   Ile   Glu   Thr   His
                                20                            25                            30

Arg   Ala   Asn   Phe   Pro   Gly   Met   Ser   Ile   Cys   Thr   Asp   Ile   Arg   Asp   Phe
                          35                            40                            45

Val   Asp   Phe   Pro   Ser   Ala   Asp   Val   Val   Val   Gly   Gly   Pro   Pro   Cys   Gln
                    50                            55                                  60

Gly   Phe   Ser   Arg   Leu   Gly
        65                            70
```

( 2 ) INFORMATION FOR SEQ ID NO:31:

( i ) SEQUENCE CHARACTERISTICS:
        ( A ) LENGTH: 48 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:31:

```
GGAGGTTAAC   ATATGCACGA   CGAACTGTTT   CCTATTCCGG   AGCCATTG                    48
```

( 2 ) INFORMATION FOR SEQ ID NO:32:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown (i i) MOLECULE TYPE: DNA (genomic)

(x i) SEQUENCE DESCRIPTION: SEQ ID NO:32:

GATGTTGTCG ACGGAGGTCC CCCATGC 27

(2) INFORMATION FOR SEQ ID NO:33:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:33:

ATGACCGACG AGTTGTTTCC TATCCCGGAG CCATTGGTC 39

(2) INFORMATION FOR SEQ ID NO:34:

(i) SEQUENCE CHARACTERISTICS:
        (A) LENGTH: 13 amino acids
        (B) TYPE: amino acid
        (C) STRANDEDNESS: unknown
        (D) TOPOLOGY: unknown (i i) MOLECULE TYPE: protein (x i) SEQUENCE DESCRIPTION: SEQ ID NO:34:

Met Thr Asp Glu Leu Phe Pro Ile Pro Glu Pro Leu Val
1               5                   10

(2) INFORMATION FOR SEQ ID NO:35:

(i) SEQUENCE CHARACTERISTICS:
        (A) LENGTH: 46 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:35:

TAGGATCCGG AGGTTTAAAA TATGACCGAC GAGCTGTTTC CTATCC 46

(2) INFORMATION FOR SEQ ID NO:36:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (i i) MOLECULE TYPE: DNA (genomic)

(x i) SEQUENCE DESCRIPTION: SEQ ID NO:36:

TAAGGATCCT CTAGAGCAGG TCGG 24

(2) INFORMATION FOR SEQ ID NO:37:

(i) SEQUENCE CHARACTERISTICS:
        (A) LENGTH: 6 amino acids
        (B) TYPE: amino acid
        (C) STRANDEDNESS: unknown
        (D) TOPOLOGY: unknown (i i) MOLECULE TYPE: protein (x i) SEQUENCE DESCRIPTION: SEQ ID NO:37:

```
      Phe  Ala  Gly  Ile  Gly  Gly
      1                        5
```

( 2 ) INFORMATION FOR SEQ ID NO:38:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:38:

```
      Phe  Ser  Gly  Ala  Gly  Gly
      1                        5
```

( 2 ) INFORMATION FOR SEQ ID NO:39:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:39:

```
      Phe  Ser  Gly  Cys  Gly  Gly
      1                        5
```

( 2 ) INFORMATION FOR SEQ ID NO:40:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:40:

```
      Ala  Gly  Phe  Pro  Cys  Gln
      1                        5
```

( 2 ) INFORMATION FOR SEQ ID NO:41:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:41:

```
      Gly  Gly  Pro  Pro  Cys  Gln
      1                        5
```

( 2 ) INFORMATION FOR SEQ ID NO:42:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:42:

```
    Ala  Gly  Phe  Pro  Cys  Gln
    1                        5
```

( 2 ) INFORMATION FOR SEQ ID NO:43:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:43:

```
    Gly  Pro  Pro  Cys  Gln
    1                   5
```

( 2 ) INFORMATION FOR SEQ ID NO:44:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:44:

```
    Glu  Asn  Val  Lys  Gly
    1                   5
```

( 2 ) INFORMATION FOR SEQ ID NO:45:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 6
        ( D ) OTHER INFORMATION: /note=""X"at Position 6 =
            Leucine/Phenylanine"

( x i ) SEQUENCE DESCRIPTION: SEQ ID NO:45:

```
    Glu  Asn  Val  Lys  Gly  Xaa
    1                   5
```

( 2 ) INFORMATION FOR SEQ ID NO:46:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:46:

```
    Gly  Asn  Ala  Val  Pro  Val
    1                   5
```

( 2 ) INFORMATION FOR SEQ ID NO:47:

( i ) SEQUENCE CHARACTERISTICS:
        ( A ) LENGTH: 4 amino acids
        ( B ) TYPE: amino acid
        ( C ) STRANDEDNESS: unknown (D) TOPOLOGY: unknown (ii) MOLECULE TYPE: protein (xi) SEQUENCE DESCRIPTION: SEQ ID NO:47:

Gly Ser Gly Thr
1

(2) INFORMATION FOR SEQ ID NO:48:

(i) SEQUENCE CHARACTERISTICS:
        (A) LENGTH: 4 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:48:

Ser Pro Pro Tyr
1

(2) INFORMATION FOR SEQ ID NO:49:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:49:

Thr Ser Pro Pro Tyr
1                5

(2) INFORMATION FOR SEQ ID NO:50:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:50:

Ser Pro Pro Tyr Trp
1                5

(2) INFORMATION FOR SEQ ID NO:51:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:51:

Val Leu Asp Pro Phe
1                5

(2) INFORMATION FOR SEQ ID NO:52:

(i) SEQUENCE CHARACTERISTICS:
        (A) LENGTH: 5 amino acids
        (B) TYPE: amino acid
        (C) STRANDEDNESS: unknown ( D ) TOPOLOGY: unknown ( i i ) MOLECULE TYPE: protein ( x i ) SEQUENCE DESCRIPTION: SEQ ID NO:52:

Gly  Ser  Gly  Thr  Thr
        1                    5

( 2 ) INFORMATION FOR SEQ ID NO:53:

( i ) SEQUENCE CHARACTERISTICS:
            ( A ) LENGTH: 5 amino acids
            ( B ) TYPE: amino acid
            ( C ) STRANDEDNESS: unknown
            ( D ) TOPOLOGY: unknown ( i i ) MOLECULE TYPE: protein ( x i ) SEQUENCE DESCRIPTION: SEQ ID NO:53:

Asp  Pro  Phe  Met  Gly
        1                    5

( 2 ) INFORMATION FOR SEQ ID NO:54:

( i ) SEQUENCE CHARACTERISTICS:
            ( A ) LENGTH: 5 amino acids
            ( B ) TYPE: amino acid
            ( C ) STRANDEDNESS: unknown
            ( D ) TOPOLOGY: unknown ( i i ) MOLECULE TYPE: protein ( x i ) SEQUENCE DESCRIPTION: SEQ ID NO:54:

Asp  Pro  Phe  Phe  Gly
        1                    5

( 2 ) INFORMATION FOR SEQ ID NO:55:

( i ) SEQUENCE CHARACTERISTICS:
            ( A ) LENGTH: 5 amino acids
            ( B ) TYPE: amino acid
            ( C ) STRANDEDNESS: unknown
            ( D ) TOPOLOGY: unknown ( i i ) MOLECULE TYPE: protein ( x i ) SEQUENCE DESCRIPTION: SEQ ID NO:55:

Asp  Pro  Phe  Ala  Gly
        1                    5